United States Patent
Swenson et al.

(10) Patent No.: US 6,726,649 B2
(45) Date of Patent: Apr. 27, 2004

(54) MEDICAL NEEDLE ASSEMBLIES

(75) Inventors: Jon D. Swenson, Wayne, NJ (US); Richard James Caizza, Vernon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 160 days.

(21) Appl. No.: 10/141,537

(22) Filed: May 9, 2002

(65) Prior Publication Data

US 2003/0125678 A1 Jul. 3, 2003

Related U.S. Application Data (60) Provisional application No. 60/344,126, filed on Dec. 28, 2001, and provisional application No. 60/346,999, filed on Jan. 11, 2002.

(51) Int. Cl.[7] .............................................. A61B 37/00
(52) U.S. Cl. .................. 604/46; 604/272; 604/264; 604/263; 604/111; 206/365; 606/185
(58) Field of Search ................. 604/46, 264, 272–274, 604/22, 47, 240, 243, 263, 192, 241, 111, 110, 162, 197, 115, 412–414, 57, 58, 164.01, 164.06, 164.08, 158, 160; 206/365; 600/562, 564, 567, 570, 576; 606/167, 181, 185

(56) References Cited

U.S. PATENT DOCUMENTS

| | | | | |
|---|---|---|---|---|
| 2,359,550 A | * | 10/1944 | Eroksen | 604/46 |
| 2,565,865 A | * | 8/1951 | Lipman | 604/46 |
| 3,119,391 A | | 1/1964 | Harrison | 128/221 |
| 3,194,237 A | | 7/1965 | Rubin | 128/253 |
| 3,351,059 A | * | 11/1967 | Kravitz | 604/46 |
| 3,512,520 A | | 5/1970 | Cowan | 128/2 |
| 3,766,919 A | | 10/1973 | Cloyd | |
| 3,905,371 A | | 9/1975 | Stickl et al. | 128/253 |
| 3,948,261 A | | 4/1976 | Steiner | 128/253 |
| 4,040,421 A | | 8/1977 | Young | |
| 4,240,423 A | * | 12/1980 | Akhavi | 604/272 |
| 4,654,034 A | | 3/1987 | Masters et al. | |
| 4,740,205 A | | 4/1988 | Seltzer et al. | |
| 4,753,641 A | * | 6/1988 | Vaslow | 604/274 |
| 4,781,697 A | | 11/1988 | Slaughter | |
| 4,782,841 A | * | 11/1988 | Lopez | 600/577 |
| 4,838,877 A | | 6/1989 | Massau | 604/272 |
| 5,181,524 A | | 1/1993 | Wanderer et al. | |
| 5,632,728 A | | 5/1997 | Hein | 604/46 |
| 6,059,737 A | * | 5/2000 | Crawford | 600/576 |
| D426,305 S | | 6/2000 | Hein | D24/147 |
| 6,241,710 B1 | | 6/2001 | VanTassel et al. | 604/272 |
| 6,298,541 B1 | * | 10/2001 | Newby et al. | 29/458 |
| 6,436,086 B1 | * | 8/2002 | Newby et al. | 604/507 |
| 6,440,104 B1 | * | 8/2002 | Newby et al. | 604/192 |

FOREIGN PATENT DOCUMENTS

FR         1378284         10/1963

* cited by examiner

Primary Examiner—Brian L. Casler
Assistant Examiner—Cris L. Rodriguez
(74) Attorney, Agent, or Firm—Webb Ziesenheim Logsdon Orkin & Hanson, P.C.

(57) ABSTRACT

A shielded, sterile, single-use unit dose needle assembly includes a unit dose needle with a hub and two packaging shields sealingly mated to one another encasing the hub and unit dose needle. The unit dose needle has a handle end and a patient end configured to hold a unit dose of a vaccine. The hub is fixedly attached to the unit dose needle between the handle end and the patient end. The first packaging shield extends over the patient end, and the second packaging shield extends over the handle end of the unit dose needle. The first and second packaging shields are removably attached to one another to form an air-tight sterility seal, with the unit dose needle contained within the first packaging shield.

25 Claims, 8 Drawing Sheets

MEDICAL NEEDLE ASSEMBLIES

CROSS-REFERENCE TO RELATED APPLICATIONS

This application claims priority from U.S. Provisional Patent Application Serial No. 60/344,126, filed Dec. 28, 2001 entitled "Bifurcated Needle Assembly with Needle Shielding Provision" and U.S. Provisional Patent Application Serial No. 60/346,999, filed Jan. 11, 2002 entitled "Medical Needle Assemblies".

BACKGROUND OF THE INVENTION

1. Field of the Invention

The present invention relates to medical applicator instruments and more particularly to vaccinating and testing needle assemblies.

2. Description of Related Art

Bifurcated or forked end needles are well-known for providing a simple and effective means for a doctor to administer a vaccine. During use, the bifurcated tip of the bifurcated needle is put into contact with either a dried or liquid substance which adheres to the bifurcated needle tip. The bifurcated needle tip is then put into contact with the skin of the patient who is being administered the vaccination. The skin is either scratched or pierced with the needle tip so that the vaccination material may be absorbed into the skin of the patient. An alternative method of delivering the vaccination includes placing a drop of the vaccine onto the skin of the patient and contacting the skin of the patient with the bifurcated needle tip through the drop of vaccine. Alternatively, a standard pointed needle tip may also be used when the drop of vaccine is applied directly to the skin of the patient.

The bifurcated needle is considered a significant medical advancement because it has allowed more people to be vaccinated with less serum. This has been especially important for those living in less developed areas because of the efficient and easy to use design, as well as the ease of replication.

Vaccination effectiveness, however, is reduced if the bifurcated needle is reused too many times. Moreover, reuse of such vaccination needles exposes patients to the risk of transmission of infectious diseases through percutaneous contact through the skin. Additionally, medical care workers using traditional vaccination needles are at an increased risk of exposure to infectious diseases due to the design of such needles, which makes them difficult to handle, as well as due to the repeated use of such needles.

In particular, bifurcated needles used to administer vaccinations are not traditionally sterilized or packaged in a single-use container that would enable convenient storage and subsequent use. Additionally, such needles have traditionally been difficult to handle in that they typically do not include a hub attached to the opposite end of a needle from the tip, and do not typically include any sort of shield for protection from the needle prior to and during use.

For example, U.S. Pat. No. 3,194,237 to Rubin discloses a vaccinating needle having a main shank with a pair of prongs at one end that define a slot of predetermined length, width and depth therebetween to hold an amount of liquid by capillary action. The shank of the needle is of sufficient length so that the non-prong end will function as a handle. U.S. Pat. No. 3,948,261 to Steiner discloses a reusable unit dose container for vaccines contained within a rigid receptacle, with a compressible closure for supporting a bifurcated needle bearing dried vaccine. The closure is adapted to support the needle in the container during a lyophilizing process while liquid vaccine is dried on the needle. The closure has grooves which permit the vaporized liquid from the vaccine to be withdrawn from the receptacle during lyophilizing, and can further seal the container.

Moreover, various needles have been disclosed including handle mechanisms, such as U.S. Pat. No. 3,119,391, which discloses a non-coring needle having a flange-like manipulating surface, and U.S. Pat. No. Des. 426,304, which discloses a vaccination needle with a flange-like handle. Such needles, however, do not provide effective structure for sterile packaging and for protection.

There exists a need for a safety assembly for use with a unit dose vaccination needle that is easily manufactured, that is simple to use, that is easily sterilized and maintained in a sterile condition until used, that can be safely disposed of, and that does not interfere with normal practices of bifurcated needle use.

SUMMARY OF THE INVENTION

The invention provides a sterile, single-use needle assembly for administering a unit dose of a vaccine, including a hub, a unit dose needle, and two packaging covers extending over the ends of the assembly to maintain sterility of the assembly. The unit dose needle includes an elongated body having a blunt handle end and a patient end configured to hold a unit dose of a vaccine. The hub includes a first end and a second end, and is fixedly attached to the elongated body of the unit dose needle between the patient end and the blunt handle end, with the patient end of the unit dose needle extending from the first end of the hub and the blunt handle end of the unit dose needle extending from the second end of the hub. A first packaging shield is removably attached to the first end of the hub, and a second packaging shield is removably attached to the second end of the hub, such as through a threaded engagement. The attachment between the first packaging shield and the hub forms an air-tight seal, with the unit dose needle contained within the first packaging shield in a sterile environment.

The unit dose needle may include a bifurcated needle, with the patient end including two pointed prongs which are capable of penetrating or abrading the skin of a patient. The prongs are desirably separated by a U-shaped channel capable of holding the unit dose of a vaccine, such as a liquid vaccine.

It is an advantage of the present invention that the rigid sleeve covers provide easy containment and sterility of the needle assembly prior to use. A notable advantage of the second rigid sleeve cover is that in certain embodiments it can remain connected to the second end of the hub to be used as a handle and assist the user in directing the use of the needle so as to easily and accurately administer a vaccination to a patient or to conduct testing on a patient.

DETAILED DESCRIPTION

Figure 1:
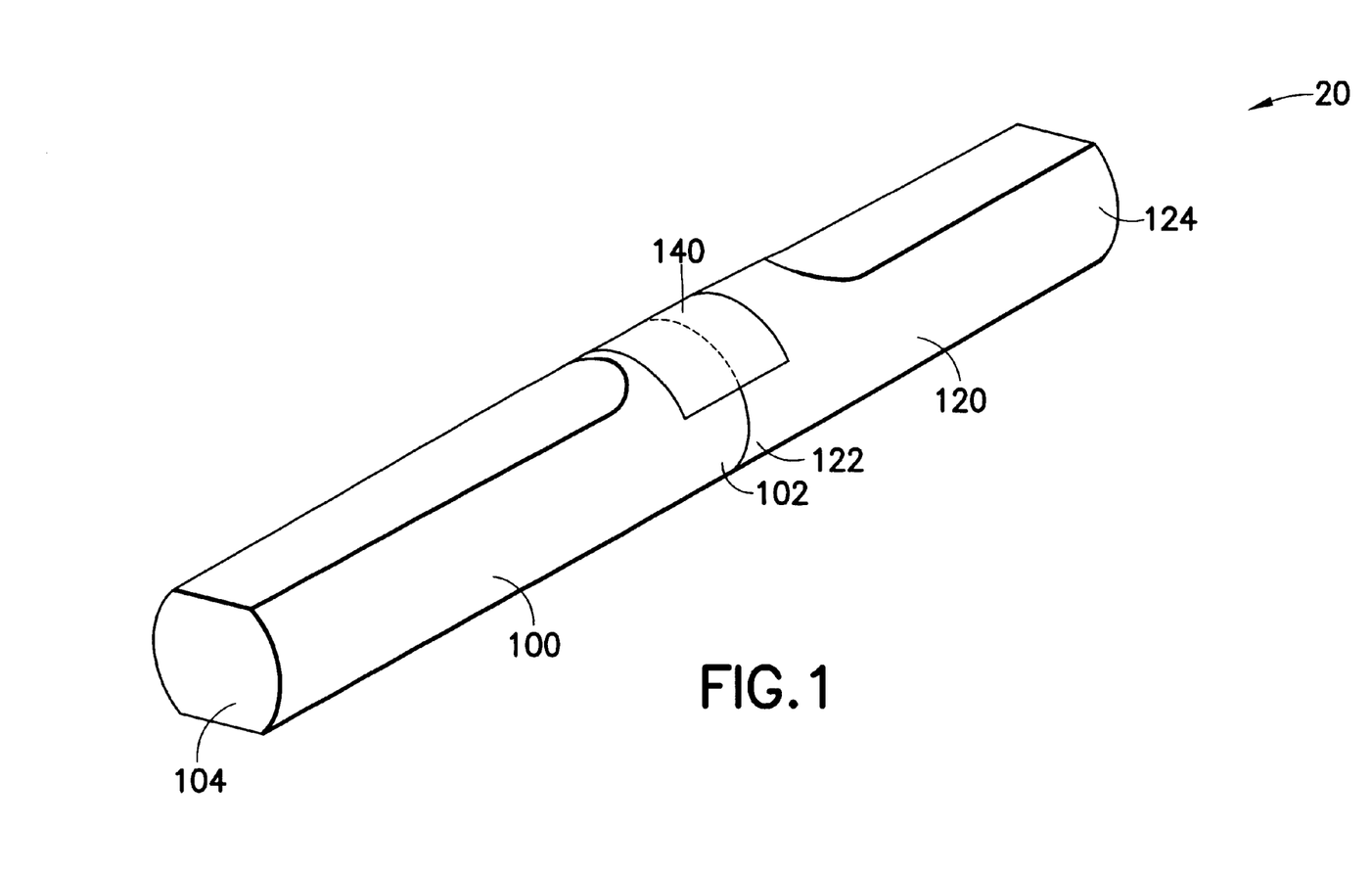
FIG. 1 is a perspective view of the needle assembly of the present invention including packaging features.

Referring to the drawings in which like reference characters refer to like parts throughout the several views thereof, FIG. 1 illustrates a fully assembled needle assembly 20 as unused and before exposure of the needle. Generally speaking, the needle assembly includes a unit dose needle 40 and a hub 60, with first and second packaging covers in the form of first rigid sleeve 100 and second rigid sleeve 120 containing the assembly in a sterile packaged form. The needle assembly 20 is intended for use for the administration of vaccines applied to or through the skin of the patient, and is intended as a single-use vaccination needle assembly including features to maintain sterility of the needle during packaging and to provide ease of use for the medical practitioner, as will be described in more detail herein.

Figure 2:
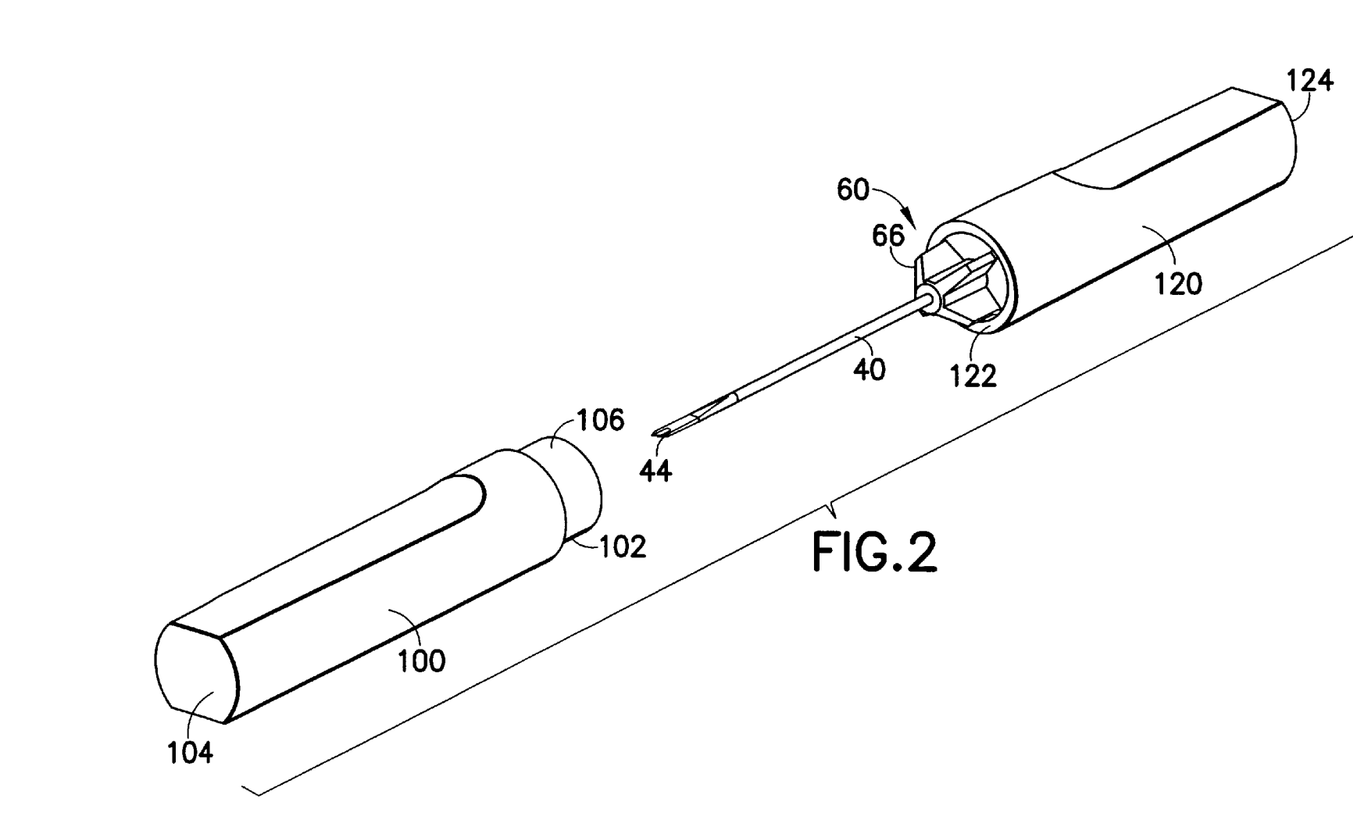
FIG. 2 is a perspective view of the needle assembly of FIG. 1 with the second rigid sleeve removed.
Figure 3:
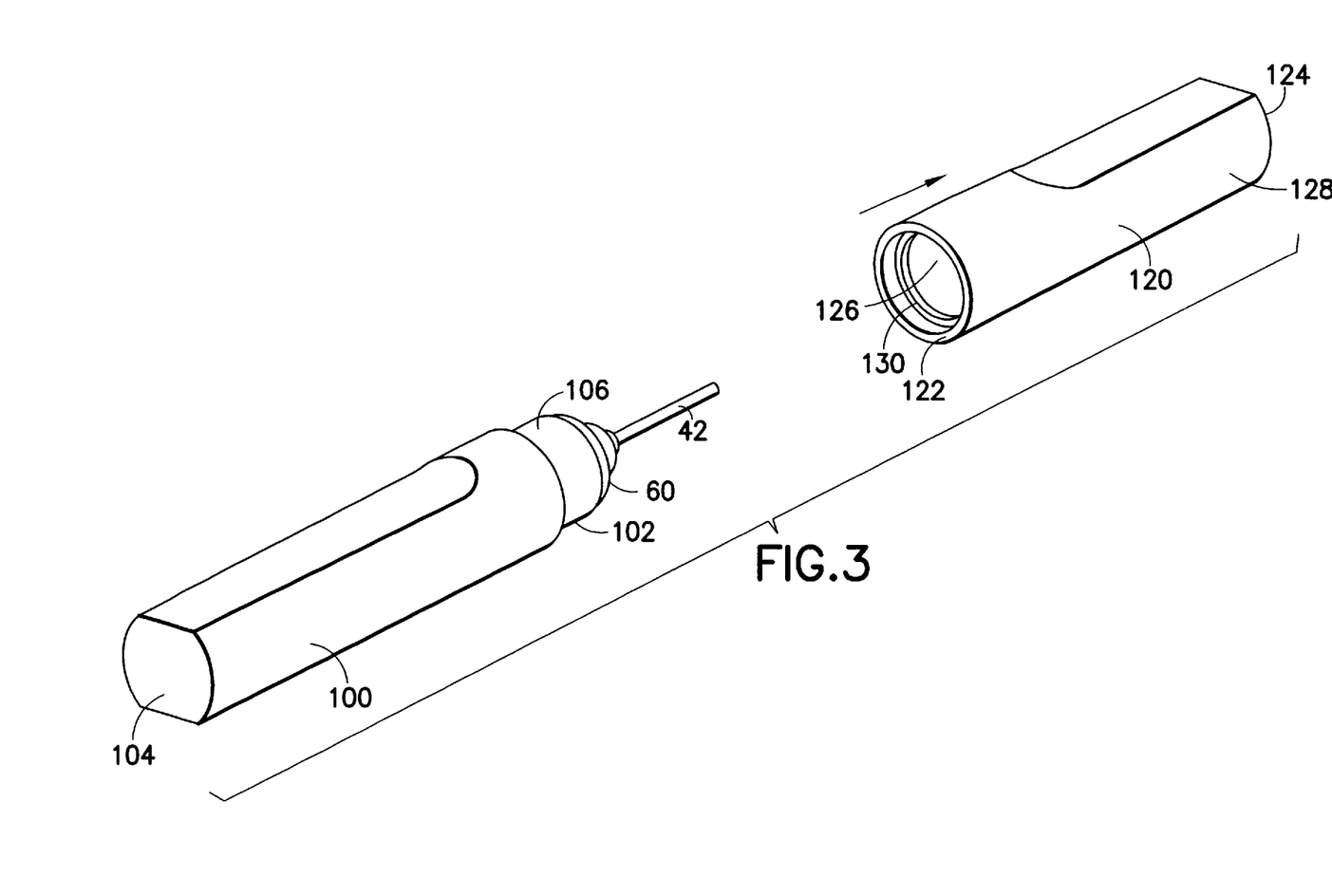
FIG. 3 is a perspective view of the needle assembly of FIG. 1 with the first rigid sleeve removed.
Figure 4:
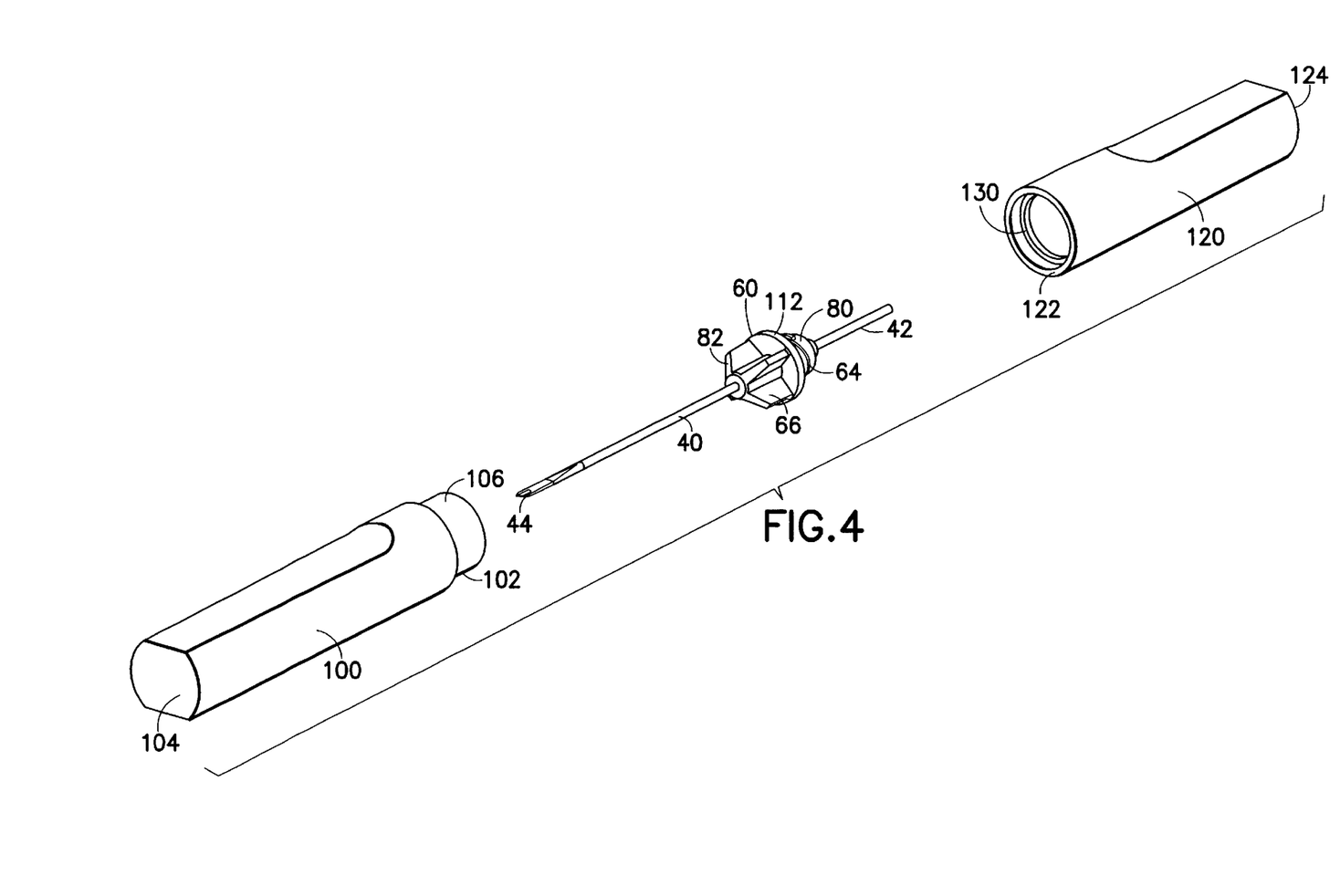
FIG. 4 is a perspective view of the needle assembly of FIG. 1 with both the first and second rigid sleeves removed.

As shown in FIGS. 2–4, needle assembly 20 includes unit dose needle 40 for administering a unit dose of a vaccine. Unit dose needle 40 may be in any form capable of administering a unit dose of a vaccine, such as in a dry powder or liquid form, as is well-known in the art. Desirably, unit dose needle 40 is in the form of a bifurcated needle including a handle end at non-patient end 42, and an opposed prong end at patient end 44. Unit dose needle 40 is provided with two sharp prongs 46 positioned at a patient end 44 of the needle. The prongs 46 are separated by a U-shaped channel 48, which is configured to hold a unit dose of vaccine, preferably in the liquid form. The prongs 46 are intended to penetrate or abrade the skin of the patient to administer the vaccine disposed in the U-shaped channel 48.

While the unit dose needle 40 is described in terms of a bifurcated needle with two prongs, unit dose needle 40 may comprise any unit dose needle capable of administering a unit dose of a vaccine, such as in a dry powder or liquid form, as is well-known in the art. Moreover, unit dose needle 40 may be constructed of any material known in the art, such as metal or plastic, and is desirably constructed of a medical grade surgical steel.

Figure 5:
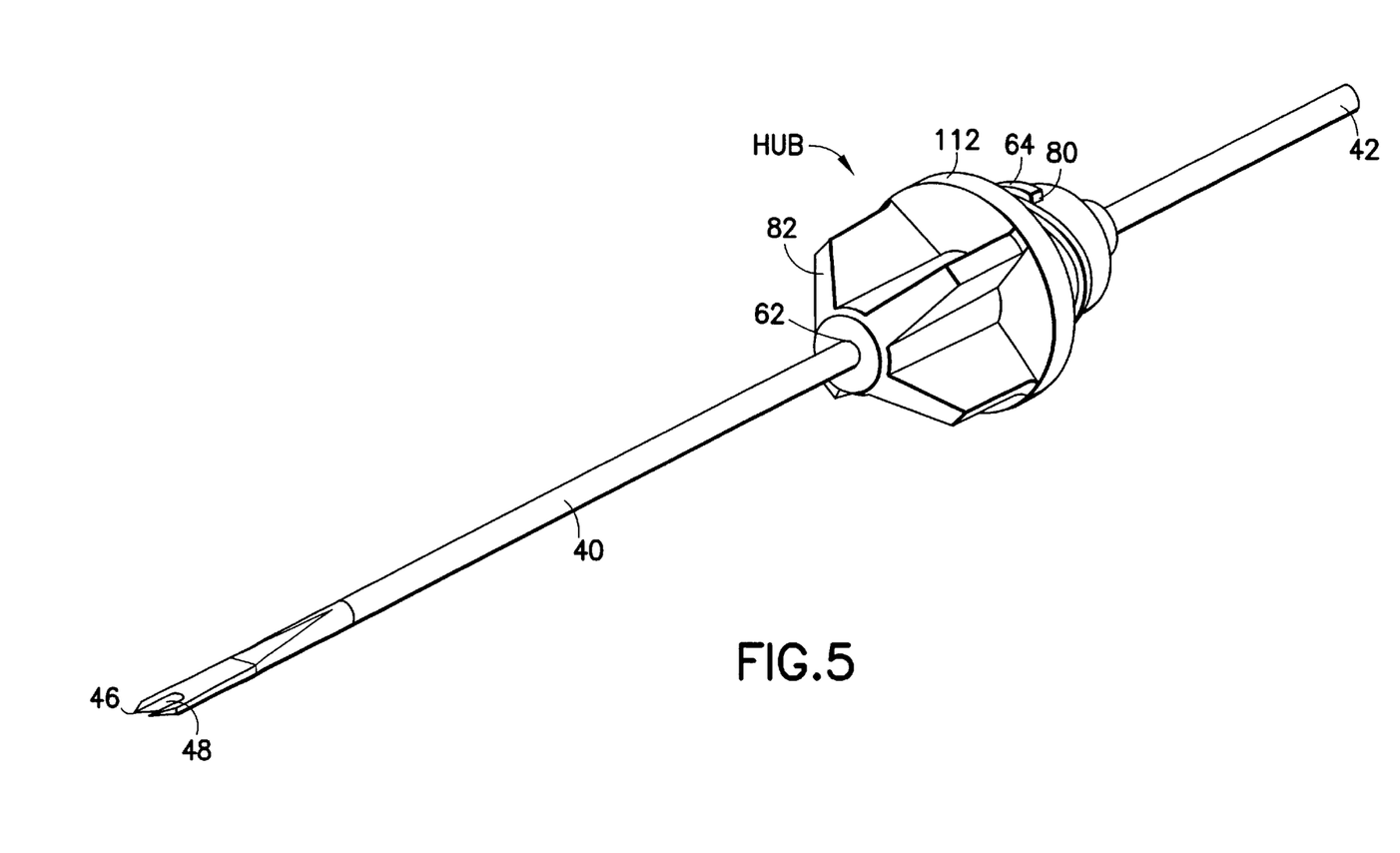
FIG. 5 is a perspective view of the unit dose needle and hub.
Figure 6:
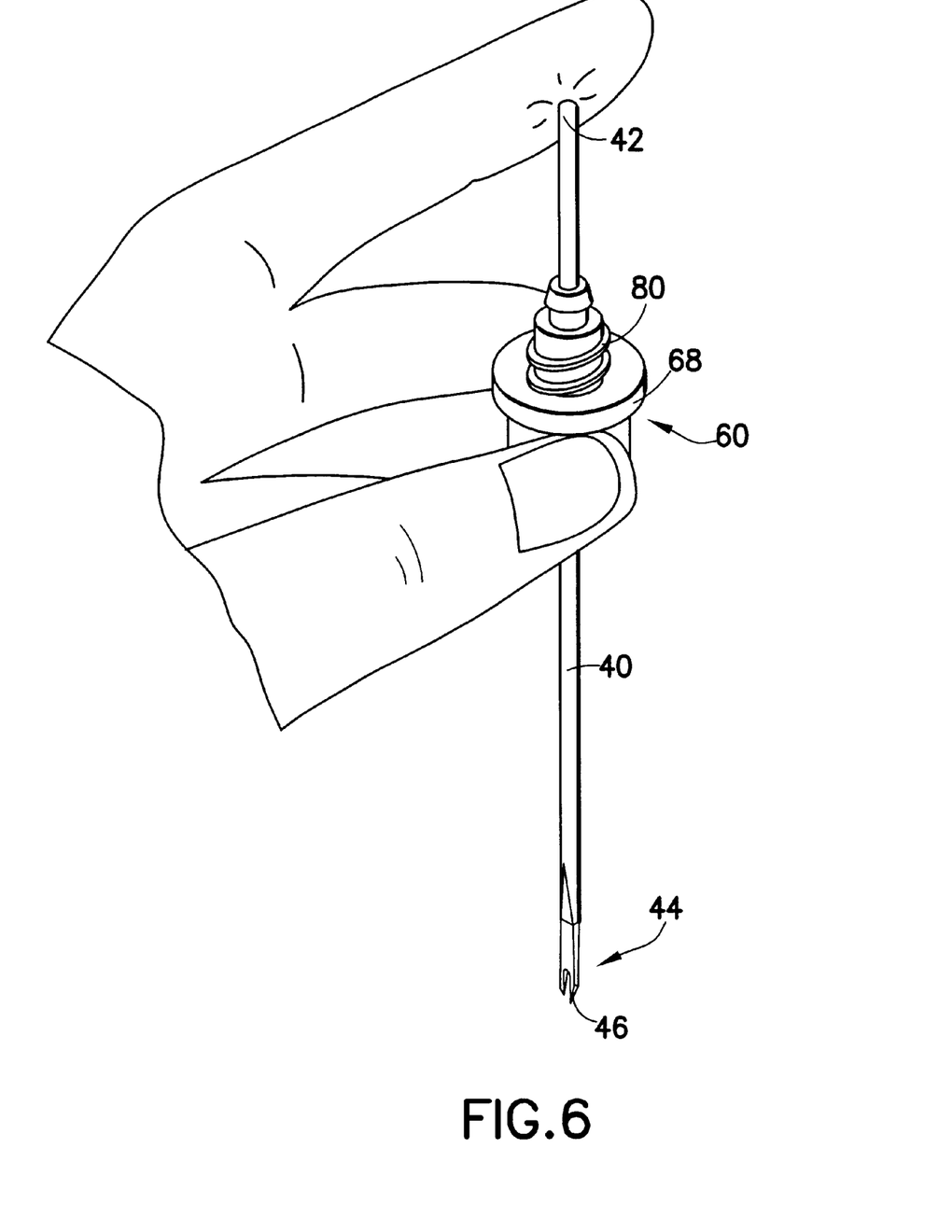
FIG. 6 is a perspective view of the unit dose needle in use.
Figure 7:
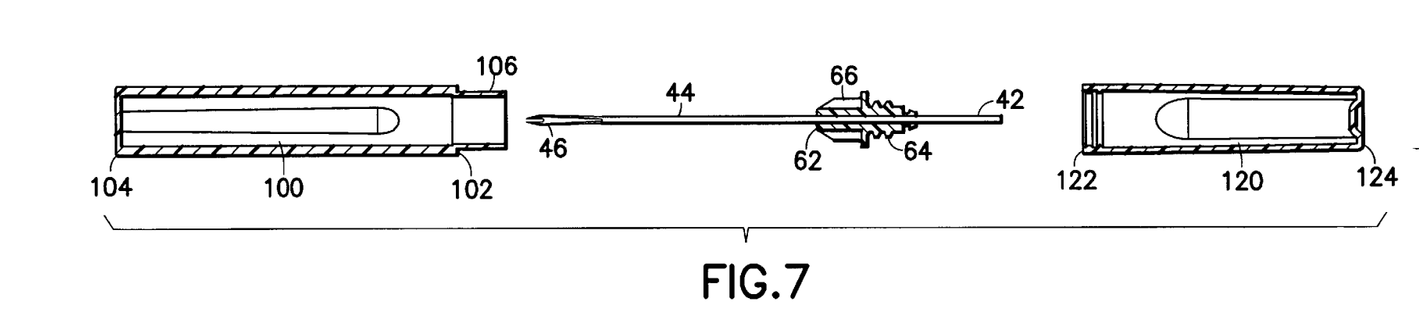
FIG. 7 is a cross-sectional view of the needle assembly in the unshielded view of FIG. 4.
Figure 8:
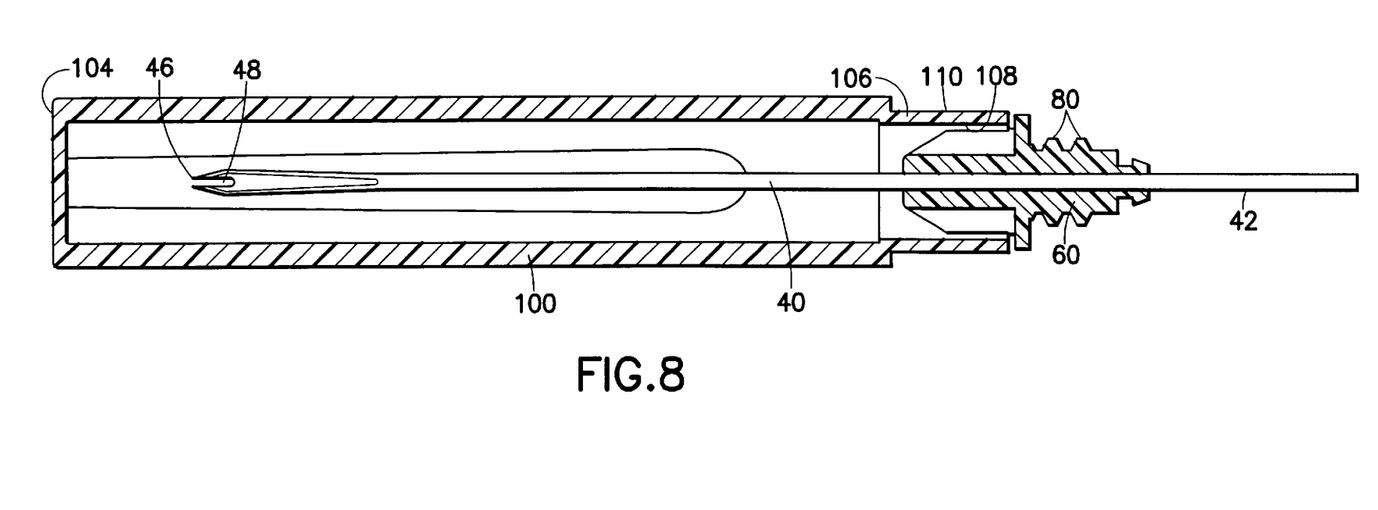
FIG. 8 is a cross-sectional view of the assembly without the second rigid sleeve.

As shown in FIGS. 4, 5 and 6, the assembly of the present invention further includes a hub 60 that includes a threaded end 64, a ribbed end 66 and passageway 62 extending between the threaded end and the ribbed end. Threaded end 64 and ribbed end 66 may be separated by a shoulder 112. In one embodiment, threaded end 64 comprises male threads 80, for threaded engagement with a rigid sleeve, as will be discussed in more detail herein. Male threads 80 further provide a structure that can be easily grasped by the user for use in administering a vaccination. Alternatively, the needle assembly may be mounted on a conventional needle holder through male threads 80 at threaded end 64, with the needle holder acting as a handle for administering a vaccination. It is noted that non-patient end 42 of unit dose needle 40 is not required when male threads 80 are used for mounting needle assembly to a conventional needle holder.

Hub 60 is affixed to unit dose needle 40 along a portion of the elongated body of unit dose needle 40 between non-patient end 42 and patient end 44. As such, non-patient end 42 of needle 40 extends from threaded end 64, and patient end 44 of needle 40 extends from ribbed end 66. Desirably, hub 60 is fixedly attached to the needle 40 through an adhesive. The adhesive may be present along the entire portion of contact between needle 40 within passageway 62, or may be present at one or both ends of passageway 62. Such an adhesive may be any material capable of fixedly attaching or adhering needle 40 to hub 60, such as an epoxy or equivalent adhesive. Desirably, internal passageway 62 includes an internal bore having an internal diameter of approximately the same size as the outer diameter of the needle 40, for accommodating and fixedly adhering needle 40 within internal passageway 62 of hub 60.

Needle assembly 20 further includes a first packaging shield in the form of a first rigid sleeve 100 extending about patient end 44 of needle 40. First rigid sleeve 100 is of a generally tubular hollow construction, including a tubular housing extending between a forward end 102 and a rearward end 104, with the tubular shape forming an internal opening extending therethrough. The forward end 102 of first rigid sleeve 100 is generally open ended, while rearward end 104 is closed ended, forming a wall. First rigid sleeve 100 extends about needle 40, thereby containing portions of needle 40 therein. More specifically, first rigid sleeve 100 extends about needle 40 thereby containing patient end 44 of needle 40.

As shown in FIGS. 2, 3, 4 and 8, first rigid sleeve 100 includes a cylindrical annular skirt 106 including an inner sidewall 108 and an outer sidewall 110. Annular skirt 106 mates with ribbed end 66 of the hub at a shoulder 112, with ribbed end 66 including male ribs 82 for a reversible friction fit insertion within annular skirt 106 of first rigid sleeve 100. Needle assembly 20 further includes a second packaging shield in the form of a second rigid sleeve 120 extending about non-patient end 42 of needle 40. Second rigid sleeve 120 is of a generally tubular hollow construction in a similar manner as first rigid sleeve 100, including a tubular housing extending between a forward end 122 and a rearward end 124, with the tubular shape forming an internal opening extending therethrough. Second rigid sleeve 120 includes an inner sidewall 126 and an outer sidewall 128. Inner sidewall 126 of second rigid sleeve 120 includes internal ribs 130 extending circumferentially along the inner sidewall of second rigid sleeve 120 adjacent the open end at forward end 122. First rigid sleeve 100 is provided to cover the patient end of the needle, and second rigid sleeve 120 is provided to cover the non-patient end. Inner sidewall 126 of second rigid sleeve 120 meets with forward end 102 of first rigid sleeve 100, with internal ribs 130 engaging annular skirt 106, forming an air-tight or hermetic seal, so as to ensure the sterility of the contents of the assembly. As such, unit dose needle 40 is contained within a sterile, air-tight structure. As shown in FIG. 1, a label 140, that may be a tamper evident label may be applied to the finally assembled parts extending between first rigid sleeve 100 and second rigid sleeve 120.

The packaging covers in the form of first rigid sleeve 100 and second rigid sleeve 120 serve to protect the unit dose needle 40 from damage and exposure to soils or other contaminants during shipping and storage, and prior to use of the needle assembly. The first rigid sleeve 100 also provides protection to medical personnel from needle sticks while removing the second rigid sleeve 120 prior to removing the first rigid sleeve 100 for administration of a vaccination. In addition, a label 140 may be applied to the finally assembled parts. The label may be used to prevent tampering of the parts, so that they are not reused. In other words, label 140 may be used as a means to indicate first rigid sleeve 100 is sealingly connected to second rigid sleeve 120.

The hub 60 and first and second rigid sleeves 100, 120 may be constructed of any material, and are desirably constructed of a moldable plastic materials. Suitable moldable plastics include, but are not limited to polyethylenes, polypropylenes, polyamides, polyesters and fluorinated polyethylenes. Preferably, hub 60 and first and second rigid sleeves 100, 120 are constructed of a rigid material.

In certain embodiments, inner sidewall 126 of second rigid sleeve 120 may have internal threads (not shown) on the inner sidewall 126 for engagement with threads 64 of hub 60, as opposed to internal ribs 130 for hermetic sealing with first rigid sleeve 100. In such embodiments, the needle assembly 20 may be assembled together whereby needle 40 is inserted through hub 60 within passageway 62 and sealed with adhesive at both sides of the hub. Then first rigid sleeve 100 may be frictionally fitted on ribs 82 of the hub 60. The second rigid sleeve 120 may be connected directly to the hub 60, whereby threads on inner sidewall 126 of second rigid sleeve 120 are threadably engaged and interconnected with male threads 80 of the hub 60. Forward end 102 of first rigid sleeve 100 meets with forward end 122 of second rigid sleeve 120 about shoulder 112, forming an air-tight seal therebetween. As described above a label 140 may be applied to the finally assembled parts. The label may be used to prevent tampering of the parts, so that they are not reused.

In use, the second packaging shield in the form of second rigid sleeve 120 is removed, such as by breaking label 140 and removing second rigid sleeve 120 from first rigid sleeve 100. Alternate embodiments may require unthreading threaded end 64 of hub 60 from female threads 130 of second rigid shield 120, thereby exposing the non-patient end 42 of unit dose needle 40. The user grasps the assembly at hub 60 between a finger and thumb, with male threads 80 acting as a gripping surface for the user. Then the first packaging shield in the form of first rigid sleeve 100 is removed, thereby exposing the two prong piercing element at patient end 44 of unit dose needle 40. Then as shown in FIG. 6, the needle assembly can be used for administration of a vaccine through the skin of a patient, using non-patient end 42 and hub 60 as a maneuverable handle for holding the assembly during use. For example, a unit dose of a vaccine contained within U-shaped channel 48 may be administered percutaneously to the patient by way of unit dose needle 40. The unit dose of the vaccine may be contained within U-shaped channel 48 during packaging and prior to removal of first rigid sleeve 100, or the unit dose of the vaccine may be placed within U-shaped channel 48 after removal of first rigid sleeve 100 immediately prior to administration. The vaccination may be administered through several applications to the patient with the same assembly. After administration of the vaccine is complete, the user may re-attach first rigid sleeve 100, thereby providing a safety shield for proper disposal of the used needle.

It is contemplated that needle assembly 20 may be used for administering a vaccination without removing second rigid sleeve 120. As such, second rigid sleeve 120 acts as a handle for the user during use. In such an embodiment, second rigid sleeve 120 may be permanently attached to hub 60, such as through an adhesive or irreversible threading means. Moreover, the hub 60 and/or the second rigid sleeve 120 may include a profile for accommodating a user's fingers.

As noted, first rigid sleeve 100 and second rigid sleeve 120 sealingly mate preferably to one another adjacent hub 60 to provide an air-tight connection therebetween, with unit dose needle 40 contained within the air-tight environment within first rigid sleeve 100 and optionally between both first and second rigid sleeves 100 and 120. Such an air-tight arrangement provides needle assembly 20 as a self-contained assembly, in the form of a complete, shielded, sterile, single-use unit dose needle assembly, which can be shipped in this form. Alternatively, this needle assembly 20 may be further packaged to provide additional sterility of the assembly. While the present invention is satisfied by embodiments in many different forms, there is shown in the drawings and described herein in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

What is claimed is:

1. A sterile, single-use needle assembly for administering a unit dose of a vaccine comprising:
    a hub including a first end and a second end;
    a unit dose needle having a patient end configured to hold a unit dose of a vaccine extending from said first end of said hub and a non-patient end extending from said second end of said hub;
    a first packaging shield removably encompassing said patient end of said unit dose needle; and
    a second packaging shield removably encompassing said non-patient end of said unit dose needle,
    wherein said first packaging shield and said second packaging shield form a sterile seal with the unit dose needle contained within said first packaging shield, wherein the unit dose needle comprises a bifurcated needle, with the patient end including two pointed prongs which are capable of penetrating or abrading the skin of a patient, and wherein the prongs are separated by a U-shaped channel capable of holding the unit dose of a vaccine.

2. The needle assembly of claim 1, wherein the unit dose of a vaccine is a liquid.

3. The needle assembly of claim 1, wherein the hub is fixedly attached to the unit dose needle along a portion of the unit dose needle between the patient end and the non-patient end by an adhesive joint.

4. The needle of claim 3, wherein the adhesive joint comprises an epoxy adhesive.

5. The needle assembly of claim 1, wherein the first end of the hub includes male ribs for reversible engagement with said first packaging shield.

6. The needle assembly of claim 1, wherein the second end of the hub includes threads.

7. The needle assembly of claim 1, wherein the first and second packaging shields comprise one or more moldable plastics.

8. The needle assembly of claim 1, further comprising a packaging label extending over an outer surface between the first packaging shield and the second packaging shield.

9. A sterile needle assembly for administering a unit dose of a vaccine comprising:
    a unit dose needle having an elongated body including a blunt handle end and a patient end configured to hold a unit dose of a vaccine;
    a hub fixedly attached to the elongated body of the unit dose needle between the patient end and the blunt handle end;
    a first packaging shield encompassing the patient end of the unit dose needle and removably attached to the hub; and
    a second packaging shield encompassing the blunt handle end of the unit dose needle and removably attached to the hub, wherein the attachment between the first packaging shield and the hub forms a sterile seal, with the unit dose needle contained within the first packaging shield, wherein the unit dose needle comprises a bifurcated needle, with the patient end including two pointed prongs which are capable of penetrating or abrading the skin of a patient, and wherein the prongs are separated by a U-shaped channel capable of holding the unit dose of a vaccine.

10. The needle assembly of claim 9, wherein the hub includes male ribs for engagement with said first packaging shield.

11. The needle assembly of claim 9, wherein the hub includes threads.

12. The needle assembly of claim 9, further comprising a packaging label extending over an outer surface between the first packaging shield and the second packaging shield.

13. A sterile needle assembly for administering a unit dose of a vaccine comprising:
- a unit dose needle having an elongated body including a non-patient end and a patient end configured to hold a unit dose of a vaccine;
- a hub fixedly attached to the elongated body of the unit dose needle having a first end and a second end;
- a first packaging shield encompassing the patient end of the unit dose needle and removably attached to said first end of said hub; and
- a second packaging shield attached to the second end of the hub,
- wherein the attachment between the first packaging shield and the hub forms a sterile seal, with the unit dose needle contained within the first packaging shield, wherein the unit dose needle comprises a bifurcated needle, with the patient end including two pointed prongs which are capable of penetrating or abrading the skin of a patient, and wherein the prongs are separated by a U-shaped channel capable of holding the unit dose of a vaccine.

14. The needle assembly of claim 13, wherein the non-patient end of the unit dose needle extends into the second packaging shield.

15. A sterile needle assembly for administering a unit dose of a vaccine comprising:
- a unit dose needle having an elongated body including a blunt handle end and a patient end configured to hold a unit dose of a vaccine;
- a hub fixedly attached to the elongated body of the unit dose needle between the patient end and the blunt handle end;
- a first packaging shield encompassing the patient end of the unit dose needle; and
- a second packaging shield encompassing the blunt handle end of the unit dose needle,
- wherein the unit dose needle is contained within the first packaging shield in a sterile environment, wherein the unit dose needle comprises a bifurcated needle, with the patient end including two pointed prongs which are capable of penetrating or abrading the skin of a patient, and wherein the prongs are separated by a U-shaped channel capable of holding the unit dose of a vaccine.

16. The needle assembly of claim 15, wherein the first packaging shield is removably mated with the hub.

17. The needle assembly of claim 16, wherein the hub includes ribs for engagement with the first packaging shield.

18. The needle assembly of claim 15, wherein the second packaging shield is removably mated with the first packaging shield.

19. The needle assembly of claim 18, further comprising a packaging label extending over an outer surface between the first packaging shield and the second packaging shield.

20. The needle assembly of claim 15, wherein the hub includes threads.

21. A sterile needle assembly for administering a unit dose of a vaccine comprising:
- a unit dose needle having an elongated body including a non-patient end and a patient end configured to hold a unit dose of a vaccine;
- a hub fixedly attached to the elongated body of the unit dose needle between the non-patient end and the patient end;
- a first packaging shield encompassing the patient end of the unit dose needle and removably mated with said hub; and
- a second packaging shield removably mated with the first packaging shield,
- wherein the unit dose needle is maintained within the first packaging shield in a sterile environment, wherein the unit dose needle comprises a bifurcated needle, with the patient end including two pointed prongs which are capable of penetrating or abrading the skin of a patient, and wherein the prongs are separated by a U-shaped channel capable of holding the unit dose of a vaccine.

22. The needle assembly of claim 21, wherein the non-patient end of the unit dose needle extends within the second packaging shield.

23. The needle assembly of claim 21, wherein the first packaging shield and the second packaging shield include interengaging structure for mating therebetween.

24. The needle assembly of claim 23, wherein said first packaging shield includes an annular skirt for mating within said second packaging shield.

25. The needle assembly of claim 24, wherein said second packaging shield includes internal ribs for engagement with said annular skirt of said first packaging shield.

* * * * *